(12) United States Patent
Sakurai et al.

(10) Patent No.: US 8,485,015 B2
(45) Date of Patent: Jul. 16, 2013

(54) DEGRADATION DETECTION SYSTEM FOR $NO_x$ SENSOR, AND DEGRADATION DETECTION METHOD THEREFOR

(75) Inventors: Kenji Sakurai, Gotenba (JP); Toru Kidokoro, Hadano (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 63 days.

(21) Appl. No.: 13/253,713

(22) Filed: Oct. 5, 2011

(65) Prior Publication Data

US 2012/0085143 A1 Apr. 12, 2012

(30) Foreign Application Priority Data

Oct. 7, 2010 (JP) .................................. 2010-227472

(51) Int. Cl.
*G01N 37/00* (2006.01)
(52) U.S. Cl.
USPC .......................................................... 73/1.06
(58) Field of Classification Search
None
See application file for complete search history.

(56) References Cited

U.S. PATENT DOCUMENTS

2010/0024520 A1* 2/2010 Sawada et al. ............... 73/23.31

FOREIGN PATENT DOCUMENTS

JP 2008-303759 A 12/2008

* cited by examiner

*Primary Examiner* — Robert R Raevis
(74) *Attorney, Agent, or Firm* — Gifford, Krass, Sprinkle, Anderson & Citkowski, P.C.

(57) ABSTRACT

A $NO_X$-sensor degradation detection system includes: a three-way catalyst disposed in an exhaust passageway of an internal combustion engine; a selective reduction catalyst disposed in the exhaust passageway downstream of the three-way catalyst; a $NO_X$ sensor disposed in the exhaust passageway downstream of the selective reduction catalyst; and a controller configured to execute a rich-shift process that is a process for causing air/fuel ratio of exhaust gas that flows into the three-way catalyst to become rich, and to determine that the $NO_X$ sensor has degraded on a condition that a measurement value from the $NO_X$ sensor does not reach nor exceed a threshold value within a prescribed time that follows start of the rich-shift process. A degradation detection method for use in the system is also provided.

12 Claims, 3 Drawing Sheets

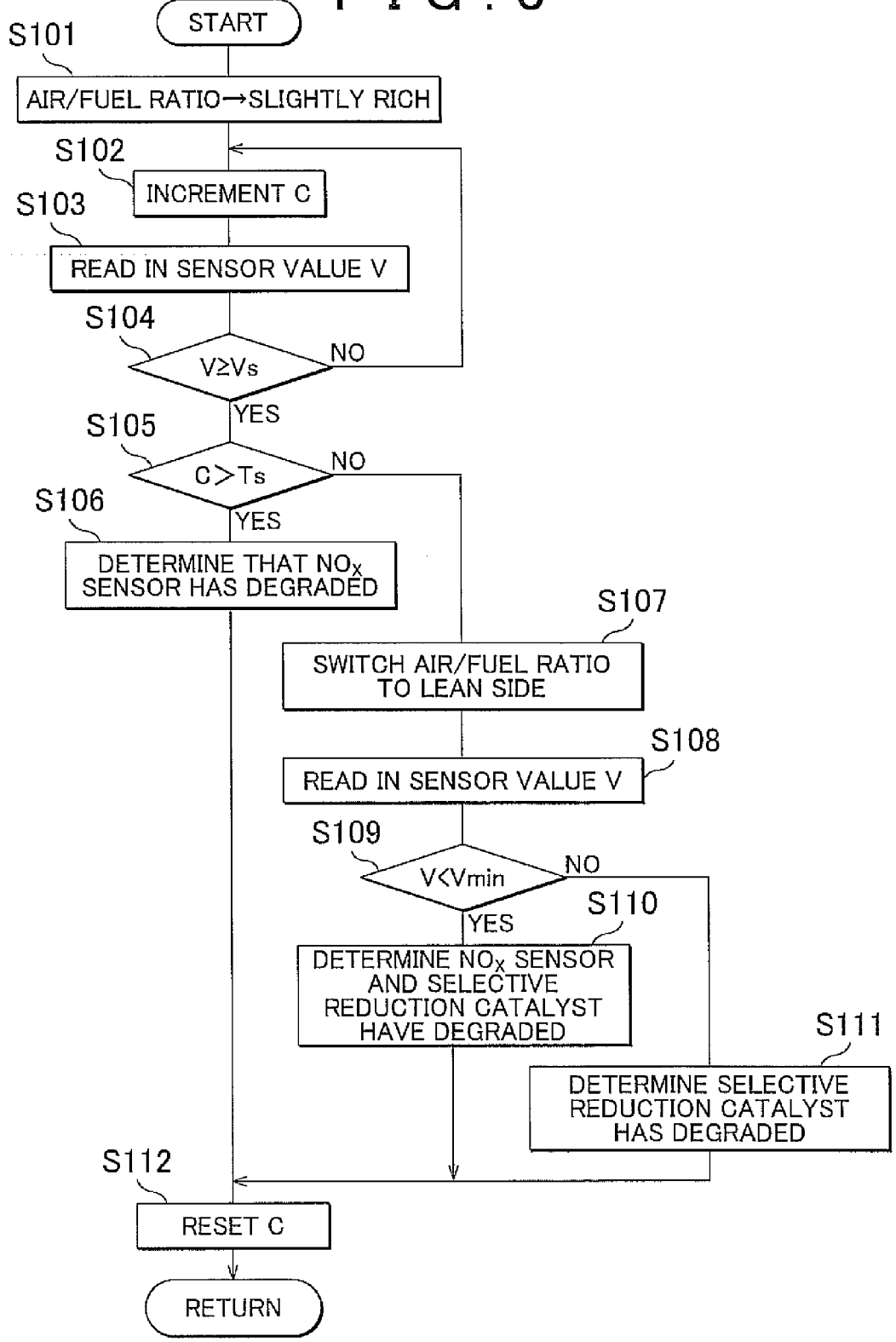

DEGRADATION DETECTION SYSTEM FOR NO$_x$ SENSOR, AND DEGRADATION DETECTION METHOD THEREFOR

CROSS REFERENCE TO RELATED APPLICATIONS

This application claims priority to Japanese Patent Application No. 2010-227472 filed on Oct. 7, 2010, which is incorporated herein by reference in its entirety including the specification, drawings and abstract.

BACKGROUND OF THE INVENTION

1. Field of the Invention

The invention relates to a technology of detecting degradation of a NO$_X$ sensor disposed downstream of an exhaust gas control apparatus that includes a three-way catalyst and a selective reduction catalyst.

2. Description of the Related Art

As a system that purifies exhaust gas of a lean-burn internal combustion engine, there is known a system in which a three-way catalyst, a storage reduction NO$_X$ catalyst and a selective reduction catalyst are disposed in that order from the upstream side (e.g., see Japanese Patent Application Publication No. 2008-303759 (JP-A-2008-303759)).

In the foregoing construction, it is conceivable to adopt a construction in which a NO$_X$ sensor is disposed in an exhaust passageway downstream of the selective reduction catalyst for the purpose of performing a feedback control of the air/fuel ratio of exhaust gas in order to keep the amount of nitrogen oxides (NO$_X$) discharged from the selective reduction catalyst to or below a target value, or detecting the degree of degradation of the selective reduction catalyst, or the like. In such a construction, it is also important to detect or determine degradation of the NO$_X$ sensor.

SUMMARY OF THE INVENTION

The invention has been accomplished in view of the foregoing circumstances, and provides a technology capable of detecting or determining degradation of the NO$_X$ sensor in a construction in which the NO$_X$ sensor is disposed in an exhaust passageway downstream of a selective reduction catalyst.

In the invention, to solve the aforementioned task, the inventors focused on a fact that the NO$_X$ sensor responds to ammonia (NH$_3$) present in exhaust gas as well as NO$_X$ present in exhaust gas.

When exhaust gas of a rich atmosphere flows into a three-way catalyst, NO$_X$ in exhaust gas is reduced by hydrocarbon (HC) or carbon monoxide (CO). At that time, nitrogen (N$_2$) in exhaust gas reacts with hydrogen (H$_2$) to produce ammonia (NH$_3$). As a result, the amount of NO$_X$ that reaches the NO$_X$ sensor is very small. On the other hand, ammonia (NH$_3$) is adsorbed to the selective reduction catalyst. Therefore, the amount of ammonia (NH$_3$) that reaches the NO$_X$ sensor is also very small. However, the adsorption capability of the selective reduction catalyst has a limit, so that after the adsorption capability of the selective reduction catalyst is saturated, the amount of ammonia (NH$_3$) that reaches the NO$_X$ sensor increases. Hence, after the adsorption capability of the selective reduction catalyst is saturated, the measurement value from the NO$_X$ sensor increases.

Therefore, a degradation detection system for a NO$_X$ sensor concerned with the invention is designed to execute a rich-shift process for causing the air/fuel ratio of exhaust gas that flows into the three-way catalyst to become a rich air/fuel ratio, and and to detect degradation of the NO$_X$ sensor by using as a parameter the time that elapses from the start of execution of the rich-shift process until the measurement value from the NO$_X$ sensor increases to or above a threshold value.

According to one aspect of the invention, there is provided a NOX sensor degradation detection system that includes: a three-way catalyst disposed in an exhaust passageway of an internal combustion engine; a selective reduction catalyst disposed in the exhaust passageway downstream of the three-way catalyst; a NOX sensor disposed in the exhaust passageway downstream of the selective reduction catalyst; and a controller configured to execute a rich-shift process that is a process for causing air/fuel ratio of exhaust gas that flows into the three-way catalyst to become rich, and to determine that the NO$_X$ sensor has degraded on a condition that a measurement value from the NOX sensor does not reach nor exceed a threshold value within a prescribed time that follows start of the rich-shift process.

According to another aspect of the invention, there is provided a NO$_X$ sensor degradation detection method for use in an exhaust gas control apparatus that includes: a three-way catalyst disposed in an exhaust passageway of an internal combustion engine; a selective reduction catalyst disposed in the exhaust passageway downstream of the three-way catalyst; and a NOX sensor disposed in the exhaust passageway downstream of the selective reduction catalyst. This NO$_X$ sensor degradation detection method includes:

executing a rich-shift process that is a process for causing air/fuel ratio of exhaust gas that flows into the three-way catalyst to become rich; and determining that the NO$_X$ sensor has degraded on a condition that a measurement value from the NO$_X$ sensor does not reach nor exceed a threshold value within a prescribed time that follows start of the rich-shift process.

Incidentally, the "threshold value" herein is a value determined on the basis of the amount of ammonia (NH$_3$) that can reach the NO$_X$ sensor after the adsorption capability of the selective reduction catalyst is saturated (hereinafter, the amount will be referred to as "normal value"), for example, a value obtained by subtracting a margin from the aforementioned normal value. Besides, the "prescribed time" herein is a time determined on the basis of the time that is required from start of execution of the rich-shift process until the adsorption capability of the normal selective reduction catalyst is saturated (hereinafter, referred to as "saturation time"), for example, a time obtained by adding a margin to the aforementioned saturation time.

According to the NO$_X$ sensor degradation detection system and the degradation detection method, the ammonia (NH$_3$) that is left unadsorbed to the selective reduction catalyst reaches the NO$_X$ sensor within the prescribed time following the start of execution of the rich-shift process. As a result, if the NO$_X$ sensor is normal, the measurement value from the NO$_X$ sensor increases to or above the threshold value within the prescribed time following the start of execution of the rich-shift process. On the other hand, if the NO$_X$ sensor has degraded, the measurement value from the NO$_X$ sensor does not increase to nor above the threshold value within the prescribed time following the start of execution of the rich-shift process.

Incidentally, if the adsorption capability of the selective reduction catalyst with degradation of the selective reduction catalyst, the timing at which the measurement value from the NO$_X$ sensor begins to increase becomes earlier. Therefore, in the case where the degree of degradation of the NO$_X$ sensor is small, there is a possibility of the measurement value from the $NO_X$ sensor increasing to or above the threshold value within the prescribed time despite the degradation of the $NO_X$ sensor. Therefore, in the foregoing system and the method, it is permissible to execute a lean-shift process for causing the air/fuel ratio of the exhaust gas to become lean after end of the rich-shift process in the case where the timing at which the measurement value from the $NO_X$ sensor become greater than or equal to the threshold value is within the prescribed time, and it is permissible to determine that the $NO_X$ sensor has degraded if the measurement value from the $NO_X$ sensor at the time of the lean-shift process is less than a lower-limit value that is smaller than the threshold value. According to this construction, even in the case where the adsorption capability of the selective reduction catalyst has degraded, degradation of the $NO_X$ sensor is able to be detected.

In the $NO_X$ sensor degradation detection system concerned with the invention, the rich-shift process may be a process of causing the air/fuel ratio of the exhaust gas that flows into the three-way catalyst to become a slightly rich air/fuel ratio. The "slightly rich air/fuel ratio" is an air/fuel ratio that is slightly lower than the stoichiometric air/fuel ratio, and is preferably an air/fuel ratio of, for example, about 14.3, which is close to the stoichiometric air/fuel ratio. According to this construction, it becomes possible to detect degradation of the $NO_X$ sensor while restraining the increase in the fuel consumption caused by the rich-shift process and the increase in the exhaust emission caused by surplus hydrocarbon (HC).

Besides, the invention is also applicable to a construction in which the three-way catalyst, the storage reduction $NO_X$ catalyst, the selective reduction catalyst and the $NO_X$ sensor are disposed in that order from the upstream side. According to this construction, during the rich-shift process, the $NO_X$ that is left unreduced on the three-way catalyst is reduced on the storage reduction $NO_X$ catalyst, so that the amount of $NO_X$ that reaches the $NO_X$ sensor can be lessened. Furthermore, since ammonia ($NH_3$) is also produced when $NO_X$ is reduced on the storage reduction $NO_X$ catalyst, the amount of ammonia ($NH_3$) supplied to the selective reduction catalyst and the $NO_X$ sensor can be increased. As a result, it becomes possible to more certainly detect degradation of the $NO_X$ sensor.

According to the $NO_X$ sensor degradation detection system and degradation detection method, degradation of the $NO_X$ sensor can be detected or determined in a construction in which the $NO_X$ sensor is disposed in the exhaust passageway downstream of the selective reduction catalyst.

BRIEF DESCRIPTION OF THE DRAWINGS

The features, advantages, and technical and industrial significance of this invention will be described in the following detailed description of example embodiments of the invention with reference to the accompanying drawings, in which like numerals denote like elements, and wherein:

FIG. 3 is a flowchart showing a routine that an ECU executes to perform detection of degradation of the $NO_X$ sensor in the embodiment.

DETAILED DESCRIPTION OF EMBODIMENTS

Hereinafter, concrete embodiments of the invention will be described with reference to the drawings. It is to be noted that the dimensions, materials, shapes, relative arrangements, etc. of component parts mentioned in conjunction with embodiments below are not meant to limit the technical scope of the invention only to what they define, unless otherwise stated. It is to be understood that "storage (occlusion)" used herein means retention of a substance (solid, liquid, gas molecules) in the form of at least one of adsorption, adhesion, absorption, trapping, occlusion, and others.

Figure 1:
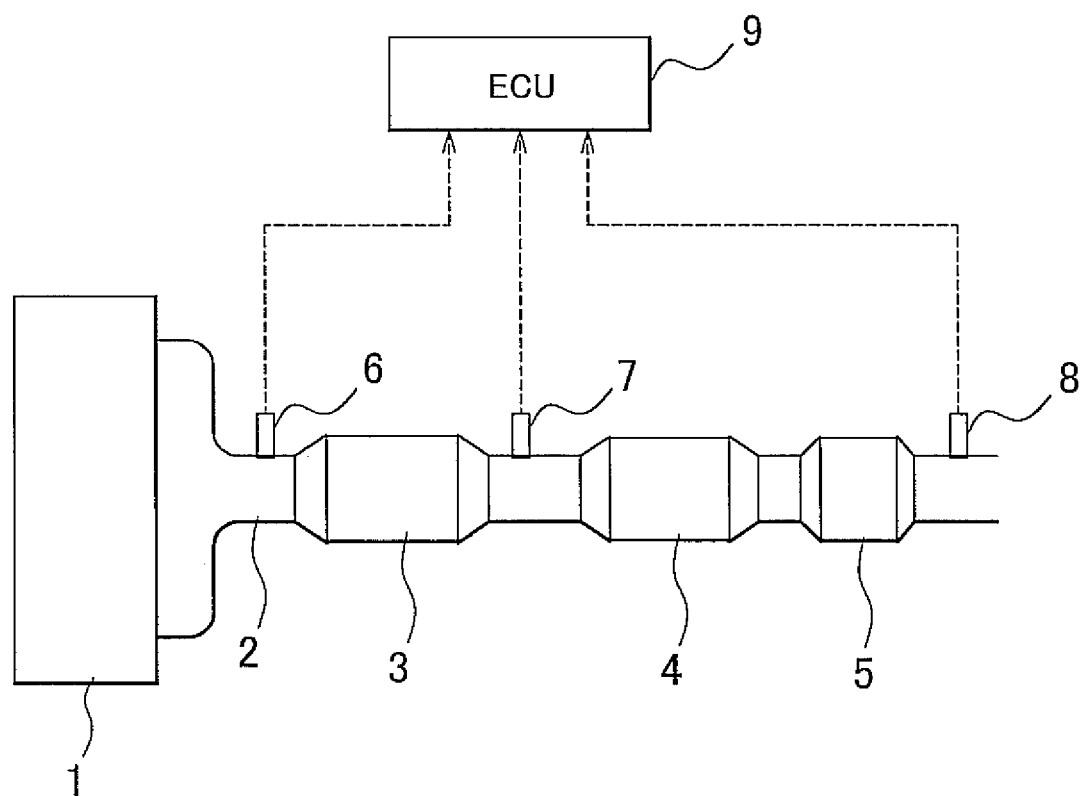
FIG. 1 is a diagram showing a general construction of an exhaust system of an internal combustion engine concerned with an embodiment of the invention.

FIG. 1 is a diagram showing a general construction of an exhaust system of an internal combustion engine to which the invention is applied. An internal combustion engine 1 shown in FIG. 1 is a compression ignition type internal combustion engine (diesel engine) or a spark ignition type internal combustion engine (gasoline engine) that is capable of burning a mixture of a lean air/fuel ratio.

An exhaust passageway 2 is connected to the internal combustion engine 1. A start converter 3 that contains a three-way catalyst is disposed on the exhaust passageway 2. A first exhaust gas control apparatus 4 that contains a storage reduction $NO_X$ catalyst is disposed on the exhaust passageway 2 downstream of the start converter 3. The storage reduction $NO_X$ catalyst, when an exhaust gas of an excess-oxygen atmosphere (lean atmosphere) flows thereinto, stores nitrogen oxides ($NO_X$) from the exhaust gas. When an exhaust gas of a reductive atmosphere (rich atmosphere) flows in, the storage reduction $NO_X$ catalyst reduces $NO_X$ by hydrocarbon (HC) or carbon monoxide (CO) from exhaust gas while releasing $NO_X$.

A second exhaust gas control apparatus 5 that contains a selective reduction catalyst is disposed on the exhaust passageway 2 downstream of the first exhaust gas control apparatus. The selective reduction catalyst, when a rich-atmosphere exhaust gas containing ammonia ($NH_3$) flows thereinto, adsorbs (stores) ammonia ($NH_3$) from the exhaust gas. When a lean-atmosphere exhaust gas flows in, the selective reduction catalyst reduces $NO_X$ in the exhaust gas by $NH_3$.

Besides, an A/F sensor 6 that measures the air/fuel ratio of exhaust gas that flows into the start converter 3 is attached to the exhaust passageway 2 upstream of the start converter 3. An $O_2$ sensor 7 that measures the concentration of oxygen contained in exhaust gas is attached to the exhaust passageway 2 between the start converter 3 and the first exhaust gas control apparatus 4. The measurement values from the A/F sensor 6 and the $O_2$ sensor 7 are input to an ECU 9. The ECU 9 is an electronic control unit for controlling the state of operation of the internal combustion engine 1 (e.g., the amount of fuel injection, the fuel injection timing, etc.) according to the measurement values from the aforementioned various sensors.

When the air/fuel ratio of exhaust gas is lean, HC and CO in the exhaust gas are oxidized by the three-way catalyst or the storage reduction $NO_X$ catalyst, and a portion of the $NO_X$ in the exhaust gas is reduced by the three-way catalyst and the rest of $NO_X$ is stored into the storage reduction $NO_X$ catalyst. Incidentally, since the amount of $NO_X$ that can be stored in the storage reduction $NO_X$ catalyst has a limit, it is necessary to reduce the $NO_X$ stored in the storage reduction $NO_X$ catalyst before the storage capability of the storage reduction $NO_X$ catalyst becomes saturated. To this end, the ECU 9 periodically executes a rich-shift process of switching the air/fuel ratio of exhaust gas from the lean side to the rich side.

When the air/fuel ratio of exhaust gas is made rich, HC and CO in exhaust gas are partially oxidized by $NO_X$ and $O_2$ in exhaust gas on the three-way catalyst, and the rest portions of the HC and the CO are oxidized on the storage reduction $NO_X$ catalyst by $NO_X$ released from the storage reduction $NO_X$ catalyst. That is, HC and CO contained in exhaust gas function as a reductant for $NO_X$ stored in the storage reduction $NO_X$ catalyst.

Incidentally, when $NO_X$ is reduced on the three-way catalyst and the storage reduction $NO_X$ catalyst, nitrogen ($N_2$) and hydrogen ($H_2$) in exhaust gas react to produce ammonia ($NH_3$). The ammonia ($NH_3$) produced on the three-way catalyst and the storage reduction $NO_X$ catalyst flows together with exhaust gas into the second exhaust gas control apparatus 5, and is therein adsorbed to the selective reduction catalyst. The ammonia ($NH_3$) adsorbed to the selective reduction catalyst reduces $NO_X$ from exhaust gas when the air/fuel ratio of exhaust gas is returned to the lean side. That is, the selective reduction catalyst reduces, by ammonia ($NH_3$), the $NO_X$ that is left unreduced or un-stored by the three-way catalyst or the storage reduction $NO_X$ catalyst. As a result, the amount of $NO_X$ and ammonia ($NH_3$) discharged into the atmosphere can be reduced as much as possible.

By the way, in the exhaust system as described above, it is desirable that a $NO_X$ sensor 8 be disposed on the exhaust passageway 2 downstream of the second exhaust gas control apparatus 5 for the purpose of performing a feedback control of the air/fuel ratio of exhaust gas in order to keep the amount of $NO_X$ discharged from the second exhaust gas control apparatus 5 to or below a target amount, or detecting the degree of degradation of the selective reduction catalyst contained in the second exhaust gas control apparatus 5, etc.

In a construction in which the $NO_X$ sensor 8 is disposed on the exhaust passageway 2 downstream of the second exhaust gas control apparatus 5, it is also necessary to detect or determine degradation of the $NO_X$ sensor 8. A degradation detection method for the $NO_X$ sensor 8 in this embodiment will be described below.

The degradation detection method for the $NO_X$ sensor 8 in this embodiment has been designed by focusing on the facts that the $NO_X$ sensor 8 responds to ammonia ($NH_3$) as well as to $NO_X$ in exhaust gas and that the selective reduction catalyst adsorbs ammonia ($NH_3$).

When the air/fuel ratio of exhaust gas discharged from the internal combustion engine 1 is made rich, $NO_X$ in exhaust gas is reduced and ammonia ($NH_3$) is produced in the start converter 3 and the first exhaust gas control apparatus 4. Therefore, the exhaust gas that flows into the second exhaust gas control apparatus 5 is a gas that scarcely contains $NO_X$ and that contains ammonia ($NH_3$). When an exhaust gas having such a property flows into the second exhaust gas control apparatus 5, ammonia ($NH_3$) in exhaust gas adsorbs to the selective reduction catalyst.

Since the adsorption capability of the selective reduction catalyst has a limit, continuation of a rich air/fuel ratio of exhaust gas results in saturation of the adsorption capability of the selective reduction catalyst. After the adsorption capability of the selective reduction catalyst is saturated, the ammonia ($NH_3$) that is left unadsorbed by the selective reduction catalyst is discharged from the second exhaust gas control apparatus 5, and reaches the $NO_X$ sensor 8. That is, before the adsorption capability of the selective reduction catalyst is saturated, the amount of ammonia ($NH_3$) that reaches the $NO_X$ sensor 8 is stable at a very low level. However, after the adsorption capability of the selective reduction catalyst is saturated, the amount of ammonia ($NH_3$) that reaches the $NO_X$ sensor 8 increases.

Figure 2:
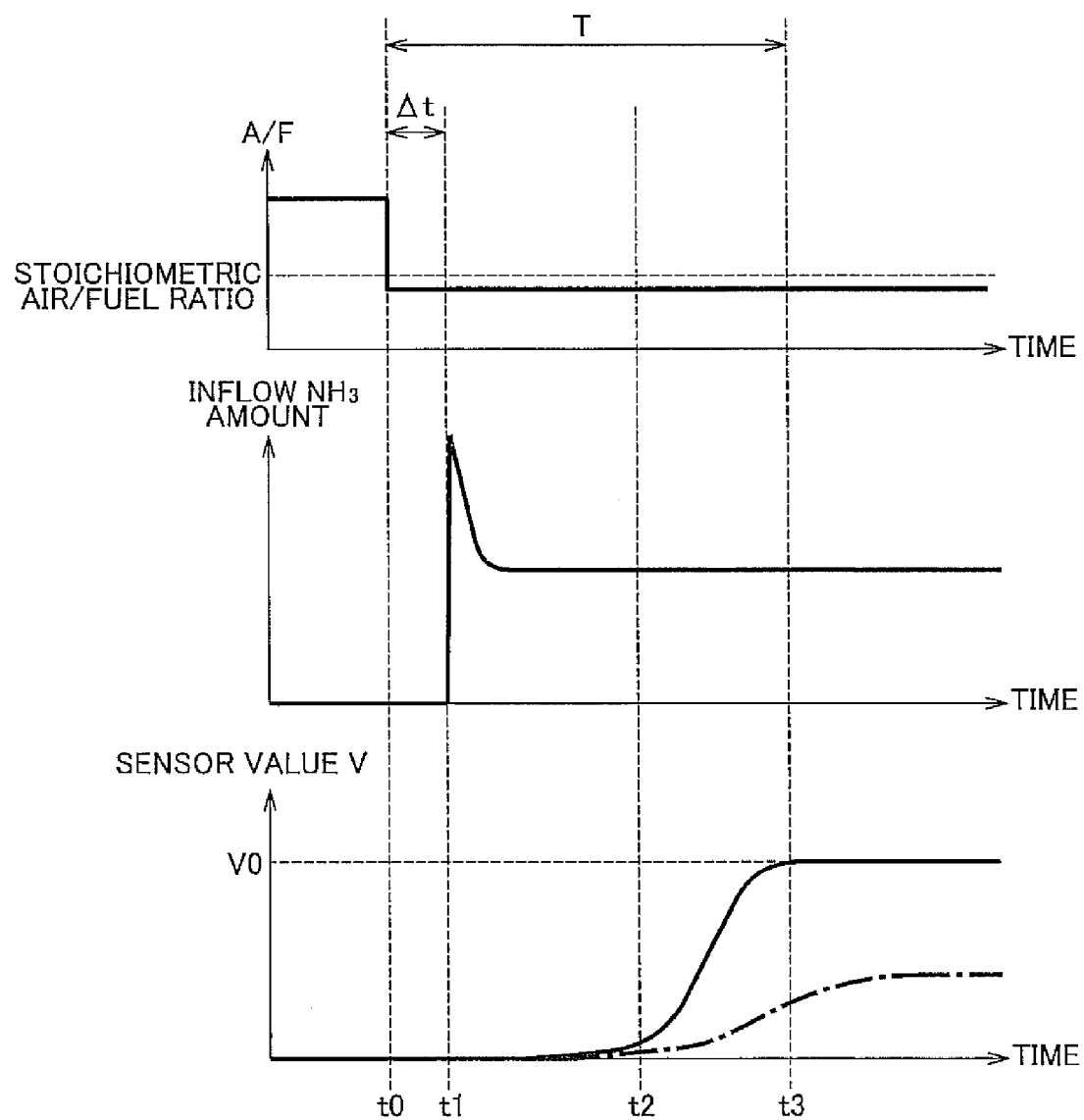
FIG. 2 is a diagram showing time-dependent changes in the amount of ammonia ($NH_3$) that flows into a second exhaust gas control apparatus and the measurement value from a $NO_X$ sensor in the case where the air/fuel ratio of exhaust gas is switched from the lean side to the rich side in the embodiment.

Time-dependent changes in the amount of ammonia ($NH_3$) (inflow $NH_3$ amount) that flows into the second exhaust gas control apparatus 5 and the measurement value from the $NO_X$ sensor 8 (sensor value V) in the case where the air/fuel ratio of exhaust gas discharged from the internal combustion engine 1 (exhaust gas that flows into the start converter 3) is switched from the lean side to the rich side are shown in FIG. 2. In FIG. 2, a solid line shows a sensor value when the $NO_X$ sensor 8 is normal, and a one-dot chain line shows the sensor value when the $NO_X$ sensor 8 has degraded.

In FIG. 2, when a transportation delay time $\Delta t$ elapses (t1 in FIG. 2) following a time point (t0 in FIG. 2) of the air/fuel ratio of exhaust gas being switched from the lean side to the rich side, the inflow $NH_3$ amount begins to increase. The "transportation delay time $\Delta t$" herein means a time that is needed for the exhaust gas discharged from the internal combustion engine 1 to reach the second exhaust gas control apparatus 5.

During a period from a time point t1 at which the inflow $NH_3$ amount begins to increase to a time point (t2 in FIG. 2) at which the adsorption capability of the selective reduction catalyst becomes saturated, the sensor value is stable substantially at zero since ammonia ($NH_3$) in exhaust gas is adsorbed to the selective reduction catalyst. After the adsorption capability of the selective reduction catalyst is saturated, the selective reduction catalyst can adsorb no more ammonia ($NH_3$). Hence, if the $NO_X$ sensor 8 is normal, the sensor value rapidly increases to a value that is slightly lower than the inflow $NH_3$ amount (to V0 in FIG. 2) (at t3 in FIG. 2). Incidentally, the sensor value V0 will be hereinafter referred to as "normal value V0". On the other hand, in the case where the $NO_X$ sensor 8 has degraded, the rate of increase of the sensor value after the adsorption capability of the selective reduction catalyst is saturated is slower than in the case where the $NO_X$ sensor 8 is normal. Furthermore, when the $NO_X$ sensor 8 has degraded, it is hard for the sensor value to increase to the normal value V0.

Therefore, in the embodiment, the rich-shift process of switching the air/fuel ratio of exhaust gas discharged from the internal combustion engine 1 from the lean side to the rich side, and it is determined that the $NO_X$ sensor 8 has degraded, on the condition that the sensor value does not reach a threshold value within a prescribed time following the start time point t0 of execution of the rich-shift process. Incidentally, the "rich-shift process" herein may be a rich-shift process for reducing the $NO_X$ stored in the storage reduction $NO_X$ catalyst, or may also be performed independently of such a rich-shift process.

The aforementioned threshold value is a value that is determined on the basis of the amount of ammonia ($NH_3$) that can reach the $NO_X$ sensor 8 after the adsorption capability of the selective reduction catalyst is saturated (i.e., a normal value V0), for example, a value Vs ($=V0-\alpha v$) obtained by subtracting a margin $\alpha v$ from the normal value V0. Besides, the aforementioned prescribed time is a time determined on the basis of the time that is required from the start of execution of the rich-shift process until the adsorption capability of the selective reduction catalyst is saturated (i.e., a saturation time), for example, a time obtained by adding a predetermined margin to the saturation time. More preferably, the aforementioned prescribed time is a value Ts ($=T+\alpha t$) obtained by adding a predetermined margin Et to a predetermined time T that is a time from t1 to t3 in FIG. 2 described above.

It is to be noted herein that the normal value V0 and the predetermined time T change according to an operation condition of the internal combustion engine 1 (e.g., the engine load or the engine rotation speed). Therefore, the aforementioned threshold value Vs and the prescribed time Ts may be found from a map whose argument is an operation condition of the internal combustion engine 1 (the engine load or the engine rotation speed). In that case, the relationship between the threshold value Vs and the engine operation condition and the relationship between the prescribed time Ts and the engine operation condition are found beforehand through adaptation processes that employ experiments and the like.

Besides, it is preferable that the air/fuel ratio exhaust gas in the aforementioned rich-shift process be adjusted to a slightly rich value of about 14.3, which is slightly smaller than a stoichiometric value. This is because if the air/fuel ratio of exhaust gas in the rich-shift process is considerably decreased from the stoichiometric air/fuel ratio, the amount of HC, CO and $NH_3$ contained in exhaust gas becomes excessively large, giving rise to a possibility of increase of the amount of HC, CO and $NH_3$ discharged into the atmosphere.

As an execution method for the rich-shift process, it is possible to use, for example, a method in which the air/fuel ratio of a mixture subjected to combustion in the internal combustion engine 1 is made slightly rich, a method in which fuel is added to exhaust gas at a certain position along a path from the combustion chamber of the internal combustion engine 1 to the start converter 3, etc.

By the way, if the adsorption capability of the selective reduction catalyst is degraded, the time from the start of execution of the rich-shift process until the sensor value reaches the threshold value Vs decreases to the aforementioned prescribed time Ts or becomes shorter than that. Therefore, in the case where the degree of degradation of the $NO_X$ sensor 8 is small, or the like, there is a possibility that the time from the start of execution of the rich-shift process until the sensor value reaches or exceeds the threshold value Vs may be within the prescribed time Ts. In that case, it becomes difficult to detect the degradation of the $NO_X$ sensor 8.

To overcome this problem, according to this embodiment, in the case where the sensor value increase to or above the threshold value Vs within the prescribed time Ts, a lean-shift process of switching the air/fuel ratio of exhaust gas from the rich side to the lean side is executed, and then if the sensor value following the execution of the lean-shift process is less than a lower-limit value, it is determined that the $NO_X$ sensor 8 has degraded. The aforementioned lower-limit value is a value that is smaller than the threshold value Vs and that is determined on the basis of a $NO_X$ amount Anox that is discharged from the selective reduction catalyst when the adsorption capability of the selective reduction catalyst has degraded, for example, a value Vmin (=Anox−αa) obtained by subtracting a predetermined margin αa from the $NO_X$ amount Anox. According to this method, degradation of the $NO_X$ sensor 8 can be detected even in the case where the selective reduction catalyst has degraded.

Hereinafter, a $NO_X$ sensor degradation detection procedure will be described with reference to FIG. 3. FIG. 3 is a flowchart showing a routine that the ECU 9 executes to detect degradation of the $NO_X$ sensor 8. This routine is a routine that is stored beforehand in a ROM of the ECU 9, or the like, and that is executed at the time of execution of the rich-shift process for reducing the $NO_X$ stored in the storage reduction $NO_X$ catalyst.

In the routine shown in FIG. 3, the ECU 9 firstly controls the internal combustion engine 1 in S101 so as to make the air/fuel ratio of exhaust gas slightly rich. As the ECU 9 executes the process of S101, the rich-shift process in this embodiment is realized.

In S102, the ECU 9 increments the value of a counter C. The counter C is a counter for measuring the elapsed time from the time point of start of execution of the rich-shift process. Subsequently in S103, the ECU 9 reads in the measurement value (sensor value) V from the $NO_X$ sensor 8. In S104, the ECU 9 determines whether or not the sensor value V read in in S103 is greater than or equal to a threshold value Vs.

If a negative determination is made in S104 (V<Vs), the ECU 9 executes the process starting at S102 again. On the other hand, if an affirmative determination is made in S104 (V≧Vs), the ECU 9 process proceeds to S105, in which the ECU determines whether or not the measured time C by the counter C has exceeded a prescribed time Ts.

If in S105 an affirmative determination is made (C>Ts), the ECU 9 process proceeds to S106, in which the ECU 9 determines that the $NO_X$ sensor 8 has degraded. In that case, the ECU 9 may turn on a warning light that is provided in a cabin of the vehicle, or may also cause a display device to display information that shows degradation of the $NO_X$ sensor 8.

On the other hand, if in S105 a negative determination is made (C≦Ts), the ECU 9 process proceeds to S107. In S107, the ECU 9 executes the lean-shift process of switching the air/fuel ratio of exhaust gas from the rich side to the lean side. In other words, the ECU 9 ends the execution of the rich-shift process in S107.

In S108, the ECU 9 reads in a measurement value (sensor value) V from the $NO_X$ sensor 8. In S109, the ECU 9 determines whether or not the sensor value V read in in S108 is smaller than a lower-limit value Vmin If in S109 an affirmative determination is made (V<Vmin), the ECU 9 process proceeds to S110, in which the ECU 9 determines that the selective reduction catalyst and the $NO_X$ sensor 8 have degraded. In that case, the ECU 9 may turn on the warning light that is provided in the cabin of the vehicle, or may also cause the display device to display information that shows degradation of the $NO_X$ sensor 8 and the selective reduction catalyst.

On the other hand, if in S109 a negative determination is made (V≧Vmin), the ECU 9 process proceeds to S111, in which the ECU 9 determines that the $NO_X$ sensor 8 is normal and that the selective reduction catalyst has degraded. In that case, the ECU 9 may turn on the warning light that is provided in the cabin of the vehicle, or may also cause the display device to display information that shows degradation of the selective reduction catalyst.

Incidentally, as the ECU 9 executes the process of S102 to S111, the determination in the embodiment is realized.

After executing the process of S106, S110 or S111, the ECU 9 process proceeds to S112, in which the ECU 9 resets the measured time of the counter C to zero.

If the detection of degradation of the $NO_X$ sensor 8 is performed according to the routine as described above, it becomes possible to detect degradation of the $NO_X$ sensor 8 regardless of the state of degradation of the selective reduction catalyst.

While the invention has been described with reference to example embodiments thereof, it is to be understood that the invention is not limited to the example described embodiments or constructions. To the contrary, the invention is intended to cover various modifications and equivalent arrangements. In addition, while the various elements of the example embodiments are shown in various combinations and configurations, other combinations and configurations, including more, less or only a single element, are also within the scope of the invention.

What is claimed is:

1. A NOX sensor degradation detection system comprising:
- a three-way catalyst disposed in an exhaust passageway of an internal combustion engine;
- a selective reduction catalyst disposed in the exhaust passageway downstream of the three-way catalyst;
- a NOX sensor disposed in the exhaust passageway downstream of the selective reduction catalyst; and
- a controller configured to execute a rich-shift process that is a process for causing air/fuel ratio of exhaust gas that flows into the three-way catalyst to become rich, and to determine that the NOX sensor has degraded on a condition that a measurement value from the NOX sensor does not reach nor exceed a threshold value within a prescribed time that follows start of the rich-shift process.

2. The NOX sensor degradation detection system according to claim 1, wherein the controller executes a lean-shift process for causing the air/fuel ratio of the exhaust gas to become lean after end of the rich-shift process when the measurement value from the NOX sensor reaches or exceeds the threshold value within the prescribed time following the start of the rich-shift process, and determines that the NOX sensor has degraded when the measurement value from the NOX sensor during execution of the lean-shift process is less than a lower-limit value that is smaller than the threshold value.

3. The NOX sensor degradation detection system according to claim 2, wherein the controller adjusts the air/fuel ratio of the exhaust gas that flows into the three-way catalyst to a slightly rich air/fuel ratio during the rich-shift process.

4. The NOX sensor degradation detection system according to claim 3, wherein the slightly rich air/fuel ratio is an air/fuel ratio whose value is about 14.3.

5. The NOX sensor degradation detection system according to claim 2, further comprising a storage reduction NOX catalyst disposed in the exhaust passageway between the three-way catalyst and the selective reduction catalyst.

6. The NOX sensor degradation detection system according to claim 1, wherein the controller adjusts the air/fuel ratio of the exhaust gas that flows into the three-way catalyst to a slightly rich air/fuel ratio during the rich-shift process.

7. The NOX sensor degradation detection system according to claim 6, wherein the slightly rich air/fuel ratio is an air/fuel ratio whose value is about 14.3.

8. The NOX sensor degradation detection system according to claim 6, further comprising a storage reduction NOX catalyst disposed in the exhaust passageway between the three-way catalyst and the selective reduction catalyst.

9. The NOX sensor degradation detection system according to claim 1, further comprising a storage reduction NOX catalyst disposed in the exhaust passageway between the three-way catalyst and the selective reduction catalyst.

10. A NOX sensor degradation detection method for use in an exhaust gas control apparatus that includes: a three-way catalyst disposed in an exhaust passageway of an internal combustion engine; a selective reduction catalyst disposed in the exhaust passageway downstream of the three-way catalyst; and a NOX sensor disposed in the exhaust passageway downstream of the selective reduction catalyst, the method comprising:
- executing a rich-shift process that is a process for causing air/fuel ratio of exhaust gas that flows into the three-way catalyst to become rich; and
- determining that the NOX sensor has degraded on a condition that a measurement value from the NOX sensor does not reach nor exceed a threshold value within a prescribed time that follows start of the rich-shift process.

11. The $NO_X$ sensor degradation detection method according to claim 10, further comprising:
- executing a lean-shift process for causing the air/fuel ratio of the exhaust gas to become lean after end of the rich-shift process when the measurement value from the $NO_X$ sensor reaches or exceeds the threshold value within the prescribed time following the start of the rich-shift process; and
- determining that the $NO_X$ sensor has degraded when the measurement value from the $NO_X$ sensor during execution of the lean-shift process is less than a lower-limit value that is smaller than the threshold value.

12. The NOX sensor degradation detection method according to claim 10, wherein the air/fuel ratio of the exhaust gas that flows into the three-way catalyst is adjusted to a slightly rich air/fuel ratio during the rich-shift process.

* * * * *